(12) United States Patent  
Nagayama et al.

(10) Patent No.: US 6,663,241 B2
(45) Date of Patent: Dec. 16, 2003

(54) VISUAL ACUITY EXAMINATION APPARATUS

(75) Inventors: Sanyo Nagayama, Tokyo (JP); Natsuki Munekata, Chiba (JP)

(73) Assignee: Neitz Instruments Co., Ltd, Shinjuku-ku (JP)

( * ) Notice: Subject to any disclaimer, the term of this patent is extended or adjusted under 35 U.S.C. 154(b) by 30 days.

(21) Appl. No.: 09/950,712

(22) Filed: Sep. 13, 2001

(65) Prior Publication Data

US 2003/0048414 A1 Mar. 13, 2003

(51) Int. Cl.⁷ .................................................. A61B 3/10
(52) U.S. Cl. ........................................................ 351/214
(58) Field of Search ................................. 351/221, 232, 351/237, 239, 242, 243, 222, 244; 396/563

(56) References Cited

U.S. PATENT DOCUMENTS 5,519,461 A * 5/1996 Kawamoto et al. ......... 351/244
5,629,748 A * 5/1997 Hayashi et al. ............. 351/232
5,870,168 A * 2/1999 Kirchhuebel et al. ....... 351/221
6,035,148 A * 3/2000 Jehan ......................... 396/563

* cited by examiner

Primary Examiner—George Manuel
(74) Attorney, Agent, or Firm—Armstrong, Kratz, Quintos, Hanson & Brooks, LLP

(57) ABSTRACT

A visual acuity examination apparatus is provided with a mark display face which has an outer face on which at least one mark is displayed so as to be viewed and which is formed such that the at least one mark and the periphery thereof are illuminated with a predetermined brightness, and a light shielding face which is disposed in front of the display face to be subjected to high speed movement, which is formed with a slit having a proper width and whose front face is formed so as to be illuminated with the same brightness as that of the mark display face. Accordingly, an accurate display contrast of the mark can be realized with a simple structure and without deterioration with age.

10 Claims, 7 Drawing Sheets

[FIG 1]
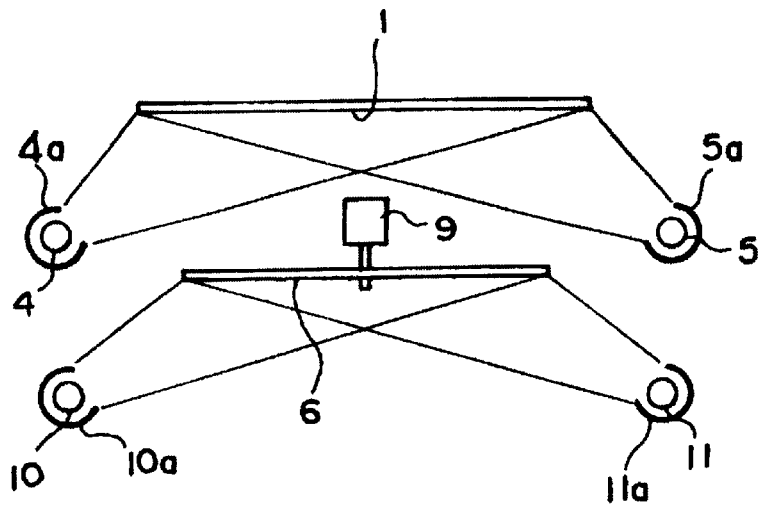
[FIG 2]
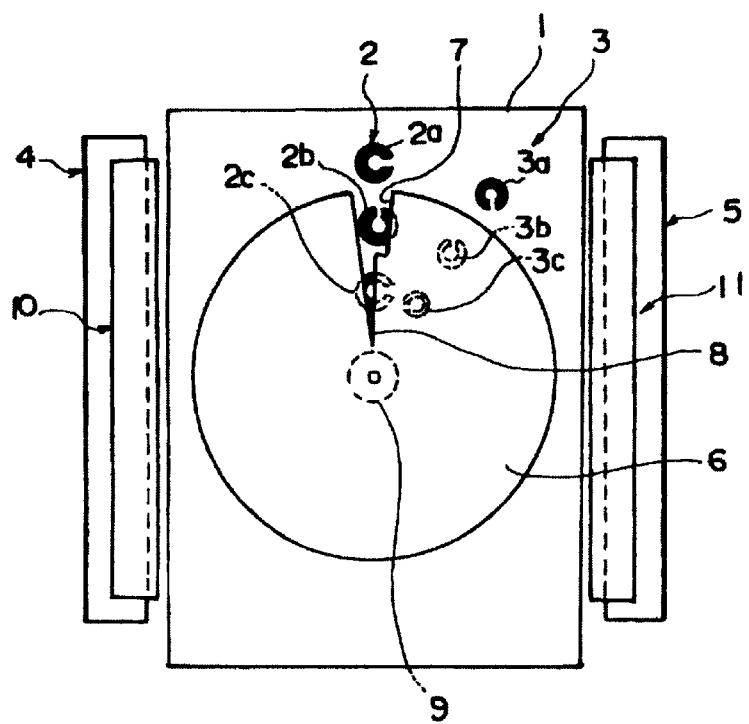

[FIG 3]
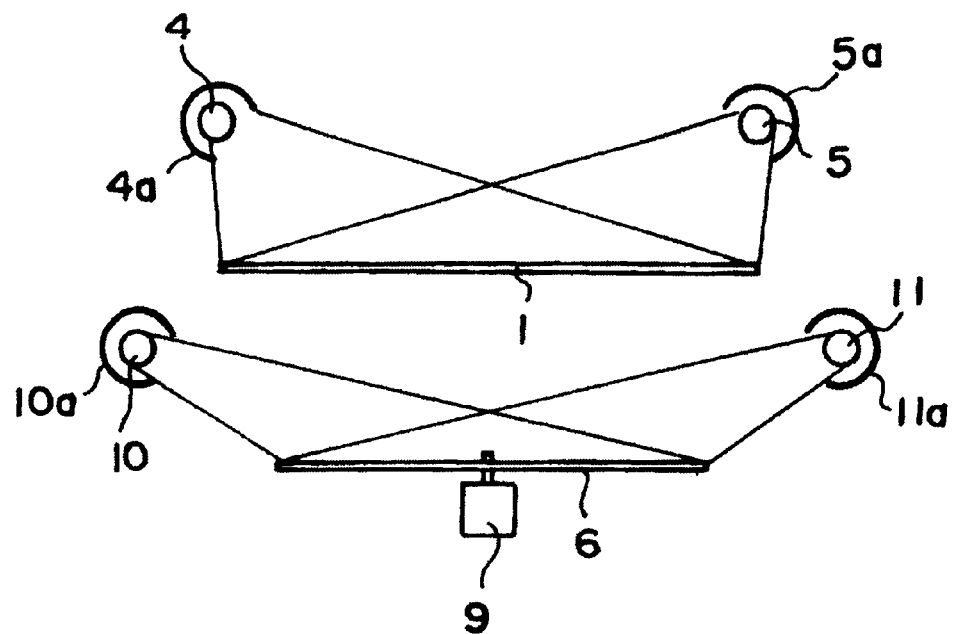

[FIG 4]
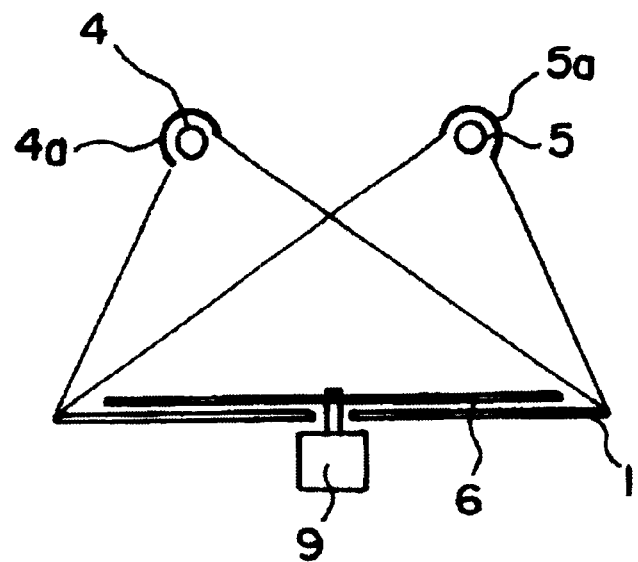

[FIG 5]
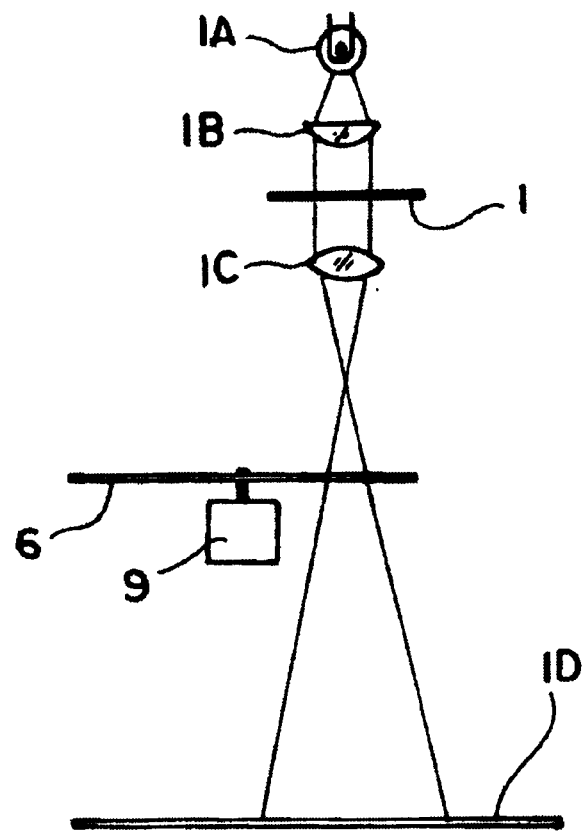

[FIG 6]
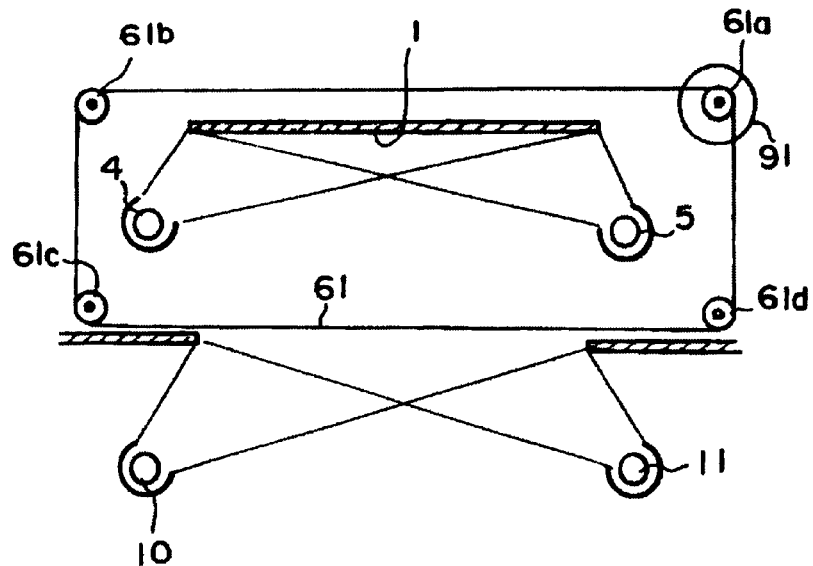
[FIG 7]
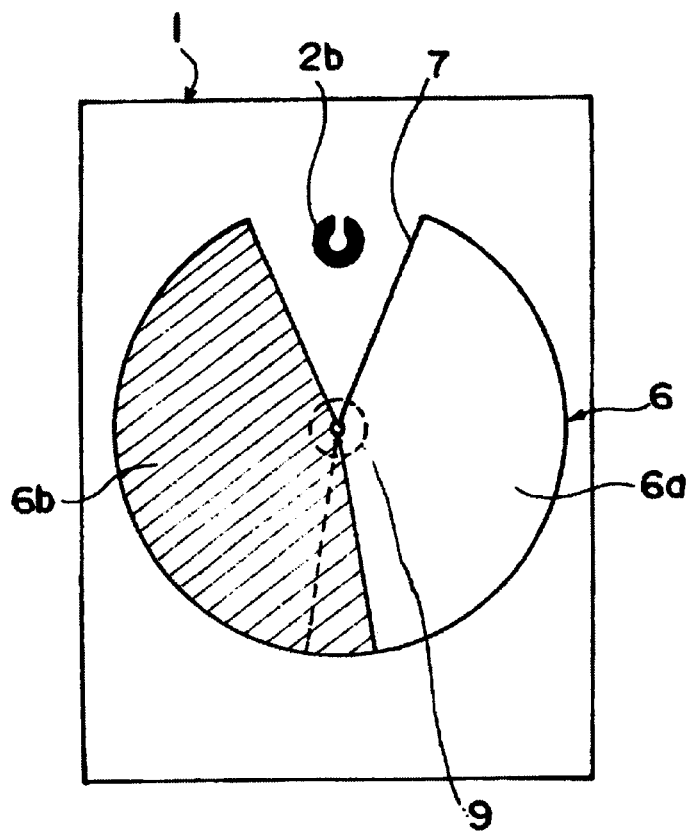

[FIG 8]
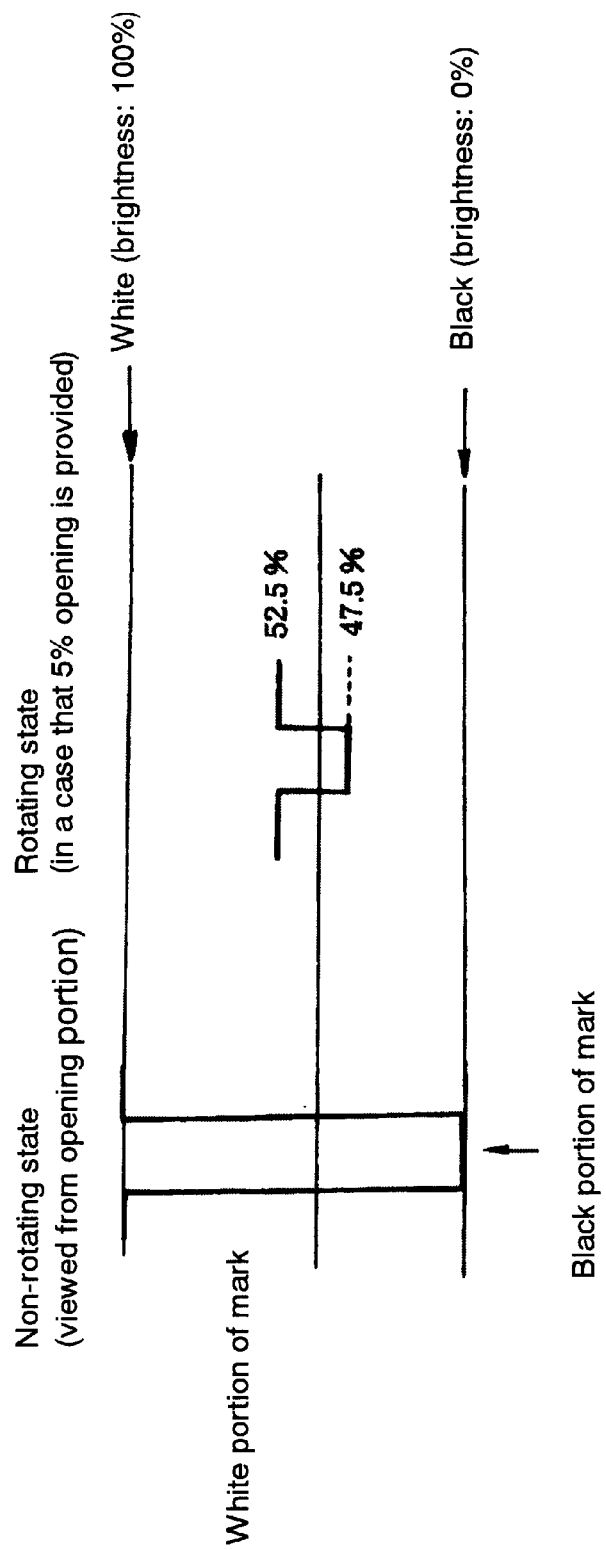

[FIG 9]
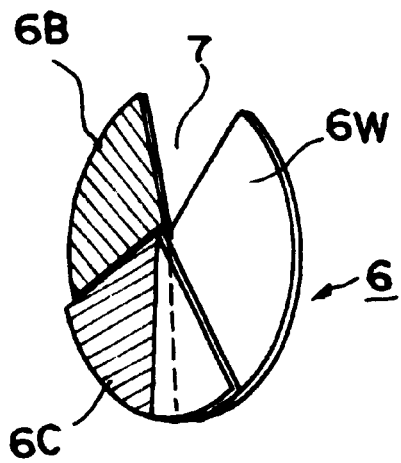
[FIG 10]
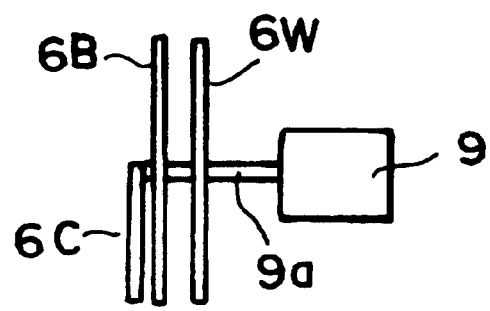

VISUAL ACUITY EXAMINATION APPARATUS

BACKGROUND OF THE INVENTION

1. Field of the Invention

The present invention relates to a visual acuity examination apparatus where the contrast of an examination mark which is viewed by a person to be examined can be set and changed accurately.

2. Description of the Related Art

In a visual acuity examination or eyesight test, there is a case where a visual acuity examination is performed by changing the contrast of a mark for examination which is displayed on a eye examination table or in an eye examination apparatus. Such a visual acuity examination is performed so as to make such a diagnosis about whether or not an eye to be examined has caught cataract. In a conventional art, however, since a displayed mark whose contrast has been changed is viewed by a person to be examined, a display mark whose display concentration or density has been controlled by a printing technique or a display mark whose contrast is changed utilizing an optical filter or a polarizing plate is used.

However, in the conventional control system for controlling the contrast of a displayed mark, a complicated structure must be employed for realizing a quantified exact contrast of a mark and it is almost impossible to maintain the set contrast without deterioration with age.

In view of the above conventional art, an object of the present invention is to provide a visual acuity examination apparatus where an exact display contrast of a mark can be realized or attained with a much simplified structure and it is hardly deteriorated with age.

According to the present invention, there is provided a visual acuity examination apparatus comprising: a mark display face which has an outer face on which at least one mark is displayed so as to be viewed and which is formed such that the at least one mark and the periphery thereof are illuminated with a predetermined brightness; and a light shielding face which is disposed in front of the mark display face so as to be moved at a high speed, which is formed with a slit having a proper width and whose front face is formed so as to be illuminated with the same brightness as that of the mark display face.

In the above structure, the present invention can be structured such that the mark display face may be formed in a polygonal shape in order to change a mark of the marks displayed on the mark display face, which should be viewed by a person to be examined, or the mark display face is formed on an endless belt entrained about left and right guide rolls and a plurality of line-shaped marks are formed on an outer surface of the belt so that the mark of each line may selectively be positioned behind the slit. Also, the high speed movement of the light shield face having the slit can be realized by rotating a member forming a light shield face, or it can be realized by traveling this light shield face member at a high speed. Furthermore, in the apparatus of the present invention, a member where at least two slits having different widths are formed on one light shield face or a member where a slit is formed such that its width can be changed may be used. Alternatively, a plurality of light shield faces which are respectively formed with different slit widths are prepared and these faces can be used in an exchanging manner.

In the present invention, regarding illumination on the light shield face and the display face, when both the faces are formed with opaque material, light source light is irradiated on the faces from their front faces, and when both the faces are formed with semi-transparent and light diffusing material, light source light is irradiated on the both the faces from their back faces. Also, the remaining face of the light shield face where no slit is formed can be colored with, for example, white and black having the same area such that, when this light shield face is rotated or run at a high speed, the brightness of the face becomes approximately half the brightness of the mark display face.

BRIEF DESCRIPTION OF THE DRAWINGS

FIG. 1 is a plan view showing a concept of a first embodiment of a basic configuration of the present invention apparatus;

FIG. 2 is a front view of the present invention apparatus shown in FIG. 1;

FIG. 3 is a plan view showing a concept of a second embodiment of the basic configuration of the present invention apparatus;

FIG. 4 is a plan view showing a concept of a third embodiment of the basic configuration of the present invention apparatus;

FIG. 5 is a plan view showing a concept of a fourth embodiment of the basic configuration of the present invention apparatus;

FIG. 6 is a plan view showing a concept of a fifth embodiment of the basic configuration of the present invention apparatus;

FIG. 7 is a plan view showing a concept of a sixth embodiment of the basic configuration of the present invention apparatus;

FIG. 8 is a contrast diagram for explaining an operation of a light shield face in the apparatus shown in FIG. 7;

FIG. 9 is a perspective view of an example of a light shield face whose slit width is made variable in the apparatus shown in FIG. 7; and FIG. 10 is a side view of the light shield face shown in FIG. 9.

DESCRIPTION OF THE PREFERRED EMBODIMENTS

Next, embodiments of a visual acuity examination apparatus according to the present invention will be explained with reference to FIGS. 1 to 3. FIG. 1 is a plan view showing a concept of a first embodiment of a basic configuration of the present invention apparatus, FIG. 2 is a front view of the present invention apparatus shown in FIG. 1, and FIG. 3 is a plan view showing a concept of a second embodiment of the basic configuration of the present invention apparatus.

In FIGS. 1 and 2, reference numeral 1 denotes a mark display face on which marks for examination 2a to 2c, 3a to 3c, and the like such as Randle rings, characters, figures are displayed by printing like an ordinary visual acuity examination paper or eyesight test chart of a printed type, and the face is made of plastic, metal or wood. Incidentally, illustration of marks other than the marks 2a to 2c and 3a to 3c is omitted in FIG. 2 for the convenience of explanation.

Reference numerals 4 and 5 denote light sources for illumination of the display plate 1 disposed on left and right sides in front of a front face of the mark display plate 1, and the display face 1 is illuminated with a predetermined brightness by operations of the light sources 4 and 5. Accordingly, as the light sources 4 and 5, ones having a light adjusting function are used for adjusting the brightness on the display face 1 obtained by the illumination.

Reference numeral 6 denotes a light shield face formed by a disk arranged on a front face side of the mark display face 1 with a proper distance therefrom. The light shield face 6 is formed with opaque material like the display face 1 and it is formed on a disk plate which has such a diameter that the inner side marks 2b, 2c, 3b and 3c of the respective marks 2a to 2c and 3a to 3c displayed on the display face 1 are covered and which is formed on the same radius line with two slits 7 and 8 having different widths. The slits 7 and 8 are formed by cutting the disk plate in a narrow fan shape so as to attain a ratio of, for example, 5% or 2.5% to the total peripheral length of the light shield face 6, and a person to be examined M can view the marks 2b, 2c and the marks 3b, 3c through the opening (slits) formed by this cutting.

The disk-shaped light shield face 6 formed with the slits 7 and 8 is provided so as to be rotatable at a high speed by mounting the center thereof to a rotation axis of a motor 9 directly or indirectly. Reference numerals 10 and 11 are light sources for illuminating the light shield face disposed in front of a front face side of the light shield face 6 on left and right outer sides thereof, and the light sources 10 and 11 are for illuminating the front face of the light shield face 6 with the same brightness as that of the mark display face 1.

In a state where a portion of the display face 1 where the marks 2 and 3 are not displayed, namely a background portion, and a front face of the light shield face 6 are illuminated by the respective light sources 4, 5 and 10, 11, and the both the light sources are adjusted such that the person to be examined M feels such that both the faces 1 and 6 are equal to each other in brightness, when the light shield face 6 is rotated at a sufficiently high speed as compared with the light-remaining time of a human eye, the marks 2b, 2c or the marks 3b, 3c appear only at a time period corresponding to the slits 7, 8, so that the time period in which the marks appear and the time period in which the marks are covered are averaged and the marks appear at a low contrast. Incidentally, all the other marks (not shown) positioned and displayed on the rotating circles of the slits 7, 8 can be viewed at this contrast by the person to be examined M.

As mentioned above, in the present invention apparatus, since the mark display face 1 and the surface the light shield face 6 with the slits 7 and 8 are illuminated to achieve the same brightness, such a specific effect can be achieved that such an accurate contrast that the difference in display brightness and brightness between the mark which is not light-shielded and the mark which has been light-shielded by intervening the slits 7 and 8 can always be kept constant can be realized, which it has been difficult to realize in the conventional visual acuity examination apparatus, and the reproducibility of the accurate contrast can be maintained for a long period of term.

Since the visual acuity examination apparatus of the present invention which can achieve such an effect can also be realized in a form illustrated in FIG. 3, the form will be explained below. In the previous embodiment, such a structure is employed that the display face 1 and the light shield face 6 are illuminated from their front sides by the light sources 4, 5 and 10, 11. In the embodiment shown in FIG. 3, however, such a structure is employed that these faces 1 and 6 are illuminated from their back side surfaces. In order to make the front side brightnesses of both the faces 1 and 6 equal to each other by the back side illumination, it is necessary to form the mark display face 1 and the light shield face 6 with semi-transparent and light diffusive material. Also, it is preferable that the motor 9 rotating the light shield face 6 is positioned on the front face side of the light shield face 6. Similarly, the visual acuity examination apparatus of the present invention can employ forms illustrated in FIGS. 4 and 5. In an embodiment shown in FIG. 4, such a structure is employed that illumination from the back side of the light sources 4 and 5 is shielded by the rotating light shielding face 6. In an apparatus shown in FIG. 5, such a form is employed that the mark display face 1 is formed in a type where marks are printed on a transparent plate with opaque ink, the marks are projected on to a screen 1D by an optical system comprising a light source for projection 1A, a condensing lens 1B, a projection lens 1C and the like, and light is shielded by inserting the light shield face 6 in a light path. The screen 1D is formed from semi-transparent and diffusive material and the person to be examined M views the marks from the back side of the screen. In this case, when the screen 1D is formed from opaque material, the projection optical system and the person to be examined M are positioned on the same side.

In the above embodiments, the light shield face 6 is formed on the disk formed with the slits 7 and 8 on the same radius line thereof. For this reason, it has been necessary to display the marks of the mark display face 1 on the mark display face 1 radially on the basis of the rotating center of the light shield face 6.

In the present invention, as shown in FIG. 6, such a form can be employed that the light shield face 6 is formed on a light shield face 61 on a light shield sheet of a belt type which runs in left and right directions (horizontal direction) or in a vertical direction, a slit with a predetermined width (a vertically longitudinal slit in the horizontally running type and a transversely longitudinal slit in the vertically running type: not shown in FIG. 6) is formed on this belt-type sheet. In this case, the marks 2 and 3 displayed on the display face 1 are displayed along the running direction of the slit. FIG. 4 is a plan view showing this configuration concept. In FIG. 6, reference numerals 61a to 61d denote rollers for supporting arrangement of the light shield face 61 of the light shield sheet and guiding running thereof, and reference numeral 91 denotes a motor for a running drive source.

Furthermore, in the present invention, such a structure (not shown) can be employed that the mark display face 1 is formed in a polygonal shape, or it is formed in a structure similar to the light shield face 61 shown in FIG. 6 and the marks positioned behind the slits of the light shield faces 6 and 61 are modified. Also, such a structure can be employed that the width of the slit of the light shield face 6 or 61 itself is made variable.

In the present invention, as illustrated in FIG. 7, such a structure can be employed that the remaining face of the previously mentioned light shield face 6 which is not provided with the slit 7 is formed so as to include a white color portion 6w and a black color portion 6b colored equally is area. Incidentally, in FIG. 7 the illumination system is omitted but it is also provided in this embodiment like the previous embodiments.

In the apparatus provided with the light shield face 6 shown in FIG. 7, an examination form such as described below can be realized. That is, the mark display face 1 is structured in a manner similar to a visual acuity table or eyesight test chart for measuring an usual visual acuity, it is printed with Randlet-rings or the like and a surface of the face 1 is illuminated by a light source (not shown) so as to attain a high contrast.

On the other hand, the disk-shaped light shield face 6 disposed in front of the front face of the display face 1 is provided with the slit 7 cut out in a fan shape such that a ratio of the slit area to the whole area is, for example, 2.5% or 5%, and a person to be examined can view the mark 2b through the slit opened.

The surface of the light shield face 6 shown in FIG. 7 is illuminated by the light source like the display face 1 and respective lights (which are not illustrated in FIG. 7) are adjusted in advance such that the background (white portion) of the mark display face 1 and a white portion of the surface of the light shield face 6 appear in the same brightness. Then, the reflectance or the like of the black portion 6b of the light shield face 6 is adjusted in advance such that the black portion 6b of the light shield face 6 appears in the same brightness as the black portion of the mark 2b of the display face 1.

When this disk-shaped light shield face 6 is rotated at a sufficiently fast speed as compared with the afterglow time of human eyes, an observing person to be examined can view the mark 2b on the surface of the display face 1 for the time of, for example, 2.5% or 5% and he/she views the surface of the rotating light shield face for the remaining time.

In this state, assuming that the brightness of the surface of the light shield face 6 is made equal to the background (a non-printed white portion) of a portion surrounding the mark 2b, when a person to be examined pays attention to a white portion (background) in the vicinity of the mark 2b, white (on the light shield face) comes into view for 47.5% of the total time, black (on the light shield face) comes into view for 47.5% thereof and white in the vicinity of the mark 2b comes into view for the remaining time of 5%, for example, in a case of the slit 7 with 5% opening. Therefore, since white enter in eye of the person as contrast for the time of 47.5+5=52.5% of the total time, assuming that the brightness of the black portion is zero, the brightness of 52.5% can be obtained as compared with a case that the person views only white in a non-rotating state. On the contrary, when the person pays attention to the black portion of the mark 2b, black comes into view for 47.5% and 5% of the total time, while white comes into view for 47.5% of the total time. Therefore, the brightness of 47.5% can be obtained like the above.

As the principle of a human eye feeling the light amount, it is known that, when lights are emitted intermittently at a high speed, the eye feels the lights in an averaged manner so that the light can be recognized as a continuous light having the brightness proportional to the time in which the lights are incident on the eye. Accordingly, when the light shield face 6 of the above embodiment is used, it is made possible to shift the amount of light incident on eye to a white side and a black side by the same amount of light on the basis of the intermediate value even when the contrast is changed as 50% of the intermediate value, and it is possible that the intermediate value of the contrast to eye is not changed. Thereby, such an ideal contrast stimulation that, while the intermediate value is kept constant, the contrast can be changed can be achieved.

FIG. 8 shows a diagram where the respective brightnesses of the colored portion (black) and the background (white) of the mark 2b in a case that the above light shield face 6 is not rotating and a case that the light shield face 6 is rotating are schematically illustrated. That is, when the light shield face 6 shown in FIG. 7 is rotated, the mark 2b (black) and the display face (background, or white) look such that the background has the brightness of 52.5%, and the mark 2b look in brightness of 47.5%. That is, light is incident on an eye in a state where the difference in brightness between the background and the mark is 5%.

FIGS. 9 and 10 show one embodiment of a type where the width of the slit 7 in the light shield face 6 on which the black portion 6b and the white portion 6w shown in FIG. 7 are applied in a separating manner is made variable, and which is formed with a black plate 6B and a white plate 6W movable about a shaft 9a, and an equally painted black and white plate 6c fixed to the shaft 9a.

According to the present invention thus structured, since a visual acuity examination apparatus of a type where an examination mark with a standard brightness and a mark with a brightness different from that of the examination mark are displayed simultaneously is structured so as to include a mark display face which has an outer face on which at least one mark is displayed so as to be viewed and which is formed such that the at least one mark and the periphery thereof are illuminated with a predetermined brightness, and a light shielding face which is disposed in front of the display face to be subjected to high speed movement, which is formed with a slit having a proper width and whose front face is formed so as to be illuminated with the same brightness as that of the mark display face, such a significant effect can be not only achieved that the contrast of the mark can easily be realized with a desired contrast but also the realized contrast can be maintained without deterioration with age.

What is claimed is:

1. A visual acuity apparatus to test the visual acuity of a person looking in a visual direction; the apparatus comprising:

a mark display face which includes an outer face on which at least one mark is displayed so as to be viewed along the visual direction and wherein the at least one mark and a periphery of the outer face of the mark display face are illuminated with a predetermined brightness; and a light shielding face which is disposed in front of the display face to be moved at a high speed, the light shielding face comprising a slit having a proper width, wherein the front face is illuminated with the same brightness as that of the mark display face; and wherein the mark display face and the light shielding face are relatively offset along the visual direction.

2. A visual acuity examination apparatus according to claim 1, wherein the mark display face is structured such that the marks which a person to be examined views is changed by moving or exchanging the mark viewed behind the slit of the light shield face.

3. A visual acuity examination apparatus according to claim 1 or 2, wherein the light shield face comprises one of a rotating body and a running body.

4. A visual acuity examination apparatus according to claim 3, wherein the light shield face formed by the rotating body is structured such that a face of the light shield face where the slit is not formed is divided into at least two equal faces on the basis of a rotation center of the rotating body, and one face of the equally divided faces is colored with a white system color and the other thereof is colored with the same color as that of the mark.

5. A visual acuity examination apparatus according to claim 3, wherein the light shield face formed by the running body is structured such that a face of the light shield face where the slit is not formed is colored to form a colored portion of a white system and another colored portion having the same color as that of the mark alternately along the running direction such that the total areas of both the colored portions are equal to each other.

6. A visual acuity examination apparatus according to claim 1, wherein the light shield face comprises at least two slits with different widths.

7. A visual acuity examination apparatus according to claim 1, wherein the light shield face comprises the slit and a width of the slit is changeable.

8. A visual acuity examination apparatus according to claim 1, wherein the light shield face comprises a plurality of faces including different slit widths formed thereon and the light shield face with a desired slit width is useable in an exchanging manner.

9. A visual acuity examination apparatus according to claim 1, wherein the mark display face is opaque.

10. A visual acuity examination apparatus according to claim 1, wherein the mark display face and the light shielding face are illuminated independently.

* * * * *